(12) United States Patent
Peter et al.

(10) Patent No.: US 9,834,814 B2
(45) Date of Patent: Dec. 5, 2017

(54) SPATIAL MOLECULAR BARCODING OF IN SITU NUCLEIC ACIDS

(71) Applicant: Agilent Technologies, Inc., Loveland, CO (US)

(72) Inventors: Brian Jon Peter, Los Altos, CA (US); Robert A. Ach, San Francisco, CA (US); Alicia Scheffer-Wong, San Jose, CA (US); Carolina Caffaro, Half Moon Bay, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 267 days.

(21) Appl. No.: 14/493,127

(22) Filed: Sep. 22, 2014

(65) Prior Publication Data
US 2015/0148239 A1 May 28, 2015

Related U.S. Application Data

(60) Provisional application No. 61/907,949, filed on Nov. 22, 2013.

(51) Int. Cl.
C12Q 1/68 (2006.01)
G01N 33/53 (2006.01)
C07H 21/00 (2006.01)

(52) U.S. Cl.
CPC .................. C12Q 1/6841 (2013.01)

(58) Field of Classification Search
CPC .............. C12Q 1/6837; C12Q 2565/50; C12Q 2565/514; G01N 33/53
See application file for complete search history.

(56) References Cited

U.S. PATENT DOCUMENTS

| | | | | |
|---|---|---|---|---|
| 7,291,471 B2* | 11/2007 | Sampson | ............. | C12Q 1/6837 435/287.2 |
| 2006/0046313 A1* | 3/2006 | Roth | ................ | G01N 33/54366 436/518 |
| 2007/0087417 A1* | 4/2007 | Namsaraev | ............. | C12N 15/10 435/91.1 |
| 2007/0099225 A1* | 5/2007 | Wilson | ............... | C12N 15/1013 435/6.12 |
| 2007/0172873 A1* | 7/2007 | Brenner | ............... | C12Q 1/6816 435/6.12 |
| 2007/0196834 A1* | 8/2007 | Cerrina | ................ | C12Q 1/6813 435/5 |
| 2007/0269870 A1* | 11/2007 | Church | ................... | C12N 15/10 435/91.2 |
| 2010/0256001 A1* | 10/2010 | Niculescu | ............ | C12Q 1/6883 506/7 |
| 2011/0104065 A1* | 5/2011 | Espina | ................... | A61K 31/22 424/9.2 |
| 2011/0172127 A1* | 7/2011 | Jacobson | ........... | C12N 15/1093 506/26 |
| 2011/0245111 A1* | 10/2011 | Chee | .................... | C12Q 1/6837 506/35 |
| 2012/0283140 A1* | 11/2012 | Chu | ..................... | B01J 19/0046 506/16 |
| 2015/0344942 A1* | 12/2015 | Frisen | ................. | C12Q 1/6837 506/2 |

FOREIGN PATENT DOCUMENTS

| | | |
|---|---|---|
| WO | WO2012140224 | 10/2012 |
| WO | WO2013150082 | 10/2013 |

OTHER PUBLICATIONS

Boal et al., Cleavage of oligodeoxyribonucleotides from controlled-pore glass supports and their rapid deprotection by gaseous amines. Nucleic Acids Research 24(15) : 3115 (1996).*

* cited by examiner

*Primary Examiner* — Ethan C Whisenant

(57) ABSTRACT

This disclosure provides, among other things, a method for analyzing a planar cellular sample. In some embodiments, the method comprises: (a) indirectly or directly attaching nucleic acid tags to binding sites in a planar cellular sample; (b) contacting the planar cellular sample with a solid support comprising an array of spatially addressed features that comprise oligonucleotides, wherein each oligonucleotide comprises a molecular barcode that identifies the feature in which the oligonucleotides is present; (c) hybridizing the nucleic acid tags, or a copy of the same, with the oligonucleotides to produce duplexes; and (d) extending the oligonucleotides in the duplexes to produce extension products that each comprises (i) a molecular barcode and (ii) a copy of a nucleic acid tag. Other embodiments, e.g., kits and the like, are also described.

17 Claims, 7 Drawing Sheets

A.

B.

C.

SPATIAL MOLECULAR BARCODING OF IN SITU NUCLEIC ACIDS

CROSS-REFERENCING

This application claims the benefit of U.S. provisional application Ser. No. 61/907,949, filed on Nov. 22, 2013, which application is incorporated by reference herein.

BACKGROUND

There is a need to combine molecular testing data with the spatial information gained from examination of tissue sections, e.g., FFPE (formalin-fixed, paraffin-embedded) tissue sections. Currently the spatial information evident in an H&E stained tissue section can be supplemented by immunohistochemical (IHC) detection of protein biomarkers. However, these methods typically provide only a semi-quantitative measurement of binding and sometimes lack resolution.

SUMMARY

Among other things, this disclosure provides a method for analyzing a planar cellular sample. In some embodiments, the method comprises: (a) indirectly or directly attaching nucleic acid tags to binding sites in a planar cellular sample; (b) contacting the planar cellular sample with a solid support comprising an array of spatially addressed features that comprise oligonucleotides, wherein each oligonucleotide comprises a molecular barcode that identifies the feature in which the oligonucleotides is present; (c) hybridizing the nucleic acid tags, or a copy of the same, with the oligonucleotides to produce duplexes; and (d) extending the oligonucleotides in the duplexes to produce extension products that each comprises (i) a molecular barcode and (ii) a copy of a nucleic acid tag.

Other embodiments, including kits, are also disclosed.

DEFINITIONS

Figure 1:
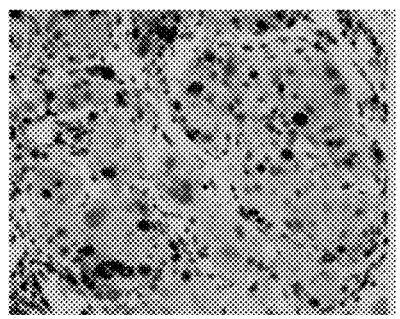
FIG. 1 schematically illustrates how array feature barcodes can be combined with FFPE sections. A: An H&E stained tissue section with informative morphology. B: An array with 30-micron features, each containing an oligonucleotide comprising a unique barcode (represented by the numbers 1, 2, 3 . . . ). C: An overlay of the array features onto the tissue section, shown to scale. Each array feature covers a small number of cells, and thus each barcode can be associated with the morphology of the cells in the H&E section.
Figure 1:
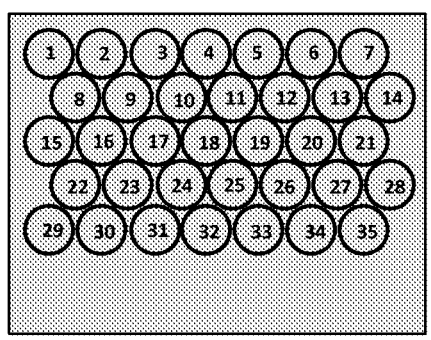
Figure 1:
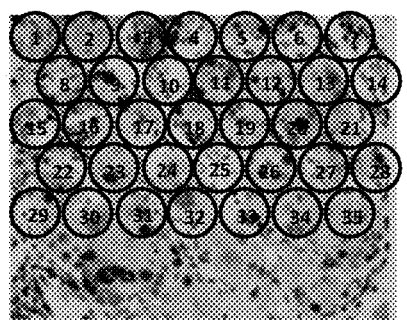

Unless defined otherwise herein, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

All patents and publications, including all sequences disclosed within such patents and publications, referred to herein are expressly incorporated by reference.

Numeric ranges are inclusive of the numbers defining the range. Unless otherwise indicated, nucleic acids are written left to right in 5' to 3' orientation; amino acid sequences are written left to right in amino to carboxy orientation, respectively.

The headings provided herein are not limitations of the various aspects or embodiments of the invention. Accordingly, the terms defined immediately below are more fully defined by reference to the specification as a whole.

Unless defined otherwise, all technical and scientific terms used herein have the same meaning as commonly understood by one of ordinary skill in the art to which this invention belongs. Singleton, et al., DICTIONARY OF MICROBIOLOGY AND MOLECULAR BIOLOGY, 2D ED., John Wiley and Sons, New York (1994), and Hale & Markham, THE HARPER COLLINS DICTIONARY OF BIOLOGY, Harper Perennial, N.Y. (1991) provide one of skill with the general meaning of many of the terms used herein. Still, certain terms are defined below for the sake of clarity and ease of reference.

A "diagnostic marker" is a specific biochemical in the body which has a particular molecular feature that makes it useful for detecting a disease, measuring the progress of disease or the effects of treatment, or for measuring a process of interest.

A "pathoindicative" cell is a cell which, when present in a tissue, indicates that the animal in which the tissue is located (or from which the tissue was obtained) is afflicted with a disease or disorder. By way of example, the presence of one or more breast cells in a lung tissue of an animal is an indication that the animal is afflicted with metastatic breast cancer. Alternatively, the infiltration of certain immune cells into a tumor may be an indication of prognosis of that tumor.

The term "epitope" as used herein is defined as small chemical groups on the antigen molecule that is bound to by an antibody. An antigen can have one or more epitopes. In many cases, an epitope is roughly five amino acids or sugars in size. One skilled in the art understands that generally the overall three-dimensional structure or the specific linear sequence of the molecule can be the main criterion of antigenic specificity.

A "subject" of diagnosis or treatment is a plant or animal, including a human. Non-human animals subject to diagnosis or treatment include, for example, livestock and pets.

As used herein, the term "labeling" refers to attaching a detectable moiety to an analyte such that the presence and/or abundance of the analyte can be determined by evaluating the presence and/or abundance of the label.

As used herein, the term "multiplexing" refers to using more than one label for the simultaneous or sequential detection and measurement of biologically active material.

A "plurality" contains at least 2 members. In certain cases, a plurality may have at least 10, at least 100, at least 100, at least 10,000, at least 100,000, at least $10^6$, at least $10^7$, at least $10^8$ or at least $10^9$ or more members.

As used herein, the term "labeling" refers to attaching a detectable moiety to specific sites in a sample (e.g., sites containing an epitope for the antibody being used) such that the presence and/or abundance of the sites can be determined by evaluating the presence and/or abundance of the label.

As used herein, the term "planar cellular sample" refers to a substantially planar, i.e., two dimensional, material that contains cells. A planar cellular sample can be made by, e.g., growing cells on a planar surface, depositing cells on a planar surface, e.g., by centrifugation, or by cutting a three dimensional object that contains cells into sections and mounting the sections onto a planar surface. The cells may be fixed using any number of reagents including formalin, methanol, paraformaldehyde, methanol:acetic acid and other reagents listed below.

As used herein, the term "tissue section" refers to a piece of tissue that has been obtained from a subject, fixed, sectioned, and mounted on a planar surface, e.g., a microscope slide.

As used herein, the term "formalin-fixed paraffin embedded (FFPE) tissue section" refers to a piece of tissue, e.g., a biopsy that has been obtained from a subject, fixed in formaldehyde (e.g., 3%-5% formaldehyde in phosphate buffered saline) or Bouin solution, embedded in wax, cut into thin sections, and then mounted on a planar surface, e.g., a microscope slide.

As used herein, the term "resin embedded tissue section" refers to a piece of tissue, e.g. a biopsy that has been obtained from a subject, fixed, (e.g., in 3-5% glutaraldehyde in 0.1M phosphate buffer), dehydrated, infiltrated with epoxy or methacrylate resin, cured, cut into thin sections, and then mounted on a planar surface, e.g., a microscope slide.

As used herein, the term "cryosection" refers to a piece of tissue, e.g. a biopsy that has been obtained from a subject, snap frozen, embedded in optimal cutting temperature embedding material, frozen, cut into thin sections and fixed (e.g. in methanol or paraformaldehyde) and mounted on a planar surface, e.g., a microscope slide.

The term "binding sites" as used herein is intended to refer to the sites, e.g., in nucleic acids and in proteins, to which the binding agents bind in a tissue section. The term "binding site" may be used synonymously with the term "epitope" in certain descriptions. In certain cases, the term "binding sites" may also refer to regions of a particular sequence or a particular structural feature in DNA or RNA.

The term "specific binding" refers to the ability of a binding agent to preferentially bind to a particular analyte that is present in a homogeneous mixture of different analytes. In certain embodiments, a specific binding interaction will discriminate between desirable and undesirable analytes in a sample, in some embodiments more than about 10- to 100-fold or more (e.g., more than about 1000- or 10,000-fold).

In certain embodiments, the affinity between a binding agent and analyte when they are specifically bound in a capture agent/analyte complex is characterized by a $K_D$ (dissociation constant) of less than $10^{-6}$ M, less than $10^{-7}$ M, less than $10^{-8}$ M, less than $10^{-9}$ M, less than $10^{-9}$ M, less than $10^{-11}$ M, or less than about $10^{-12}$ M or less.

As used herein, an "aptamer" is a synthetic oligonucleotide or peptide molecule that specifically binds to a specific target molecule.

The term "nucleic acid tag" is intended to refer to a nucleic acid that has a sequence that allows it to be distinguished from other nucleic acid tags. In embodiments in which the nucleic acid tag is an aptamer, the tag sequence is part of the aptamer. In these embodiments, the aptamer binds directly to a binding site and the nucleotide sequence of the aptamer is different to the nucleotide sequence of other aptamers (which bind to other binding sites). In embodiments in which the nucleic acid tag binds indirectly to a binding site (i.e., in embodiments in which the tag is tethered to a binding agent such as an antibody), then the nucleotide sequence of the tag for one binding agent (e.g., one antibody) is different to the nucleotide sequence of the tags that are tethered to other antibodies (which bind to other binding sites).

The term "indirectly attaching", in the context of indirectly attaching a nucleic acid tag to a binding site, is intended to mean that that the nucleic acid tag is tethered to a binding agent that binds to the binding site. In these embodiments, the binding agent binds to the binding site and the nucleic acid tag is tethered to the binding agent. The oligonucleotide tag of an oligonucleotide-tagged antibody is an example of a nucleic acid tag that indirectly binds to a binding site.

The term "directly attaching", in the context of directly attaching a nucleic acid tag to a binding site, is intended to mean that that the nucleic acid tag itself binds to the binding site. In these embodiments, the nucleic acid tag itself is a binding agent. Aptamers are examples of nucleic acid tags that directly bind to binding sites.

As used herein, the term "array" is intended to describe a two-dimensional arrangement of addressable regions bearing oligonucleotides associated with that region. The oligonucleotides of an array may be covalently attached to substrate at any point along the nucleic acid chain, but are generally attached at one terminus (e.g. the 3' or 5' terminus).

Any given substrate may carry one, two, four or more arrays disposed on a front surface of the substrate. Depending upon the use, any or all of the arrays may be the same or different from one another and each may contain multiple spots or features. An array may contain at least 10, at least 100, at least 1,000, at least 10,000, at least 100,000, or at least $10^6$ or more features, in an area of less than 20 cm$^2$, e.g., in an area of less than 10 cm$^2$, of less than 5 cm$^2$, or of less than 1 cm$^2$. In some embodiments, features may have widths (that is, diameter, for a round spot) in the range from 1 μm to 1.0 cm, although features outside of these dimensions are envisioned. In some embodiments, a feature may have a width in the range of 3.0 μm to 200 μm, e.g., 5.0 μm to 100 μm or 10 μm to 50 μm. Interfeature areas will typically be present which do not carry any polymeric compound. It will be appreciated though, that the interfeature areas, when present, could be of various sizes and configurations.

Each array may cover an area of less than 100 cm$^2$, e.g., less than 50 cm$^2$, less than 10 cm$^2$ or less than 1 cm$^2$. In some embodiments, the substrate carrying the one or more arrays will be shaped generally as a rectangular or square solid (although other shapes are possible), having a length of more than 4 mm and less than 10 cm, e.g., more than 5 mm and less than 5 cm, and a width of more than 4 mm and less than 10 cm, e.g., more than 5 mm and less than 5 cm.

Arrays can be fabricated using drop deposition from pulse jets of either polynucleotide precursor units (such as monomers) in the case of in situ fabrication, or a previously obtained polynucleotide. Such methods are described in detail in, for example, U.S. Pat. Nos. 6,242,266, 6,232,072, 6,180,351, 6,171,797, 6,323,043, U.S. patent application Ser. No. 09/302,898 filed Apr. 30, 1999 by Caren et al., and the references cited therein. These references are incorporated herein by reference. Other drop deposition methods can be used for fabrication, as previously described herein. Also, instead of drop deposition methods, photolithographic array fabrication methods may be used. Interfeature areas need not be present particularly when the arrays are made by photolithographic methods.

An array is "addressable" when it has multiple regions of different moieties (e.g., different polynucleotide sequences) such that a region (i.e., a "feature", "spot" or "area" of the array) is at a particular predetermined location (i.e., an "address") on the array. Array features are typically, but need not be, separated by intervening spaces.

The term "oligonucleotide" as used herein denotes a single-stranded multimer of nucleotide of from about 2 to 200 nucleotides, up to 500 nucleotides in length. Oligonucleotides may be synthetic or may be made enzymatically, and, in some embodiments, are 30 to 150 nucleotides in length. Oligonucleotides may contain ribonucleotide monomers (i.e., may be oligoribonucleotides) and/or deoxyribonucleotide monomers. An oligonucleotide may be 10 to 20, 21 to 30, 31 to 40, 41 to 50, 51 to 60, 61 to 70, 71 to 80, 80 to 100, 100 to 150 or 150 to 200 nucleotides in length, for example.

The term "primer" as used herein refers to an oligonucleotide, whether occurring naturally as in a purified restriction digest or produced synthetically, which is capable of acting as a point of initiation of synthesis when placed under conditions in which synthesis of a primer extension product, which is complementary to a nucleic acid strand, is induced, i.e., in the presence of nucleotides and an inducing agent such as a DNA polymerase and at a suitable temperature and pH. The primer may be either single-stranded or double-stranded and must be sufficiently long to prime the synthesis of the desired extension product in the presence of the inducing agent. The exact length of the primer will depend upon many factors, including temperature, source of primer and use of the method. For example, for some applications, depending on the complexity of the target sequence, the oligonucleotide primer may contain 15-25 or more nucleotides, although it may contain fewer nucleotides.

The term "barcode sequence" or "molecular barcode", as used herein, refers to a unique sequence of nucleotides that can be used to identify and/or track the address of a polynucleotide on a support. A barcode sequence may be at the 5'-end, the 3'-end or in the middle of an oligonucleotide. Barcode sequences may vary widely in size and composition; the following references provide guidance for selecting sets of barcode sequences appropriate for particular embodiments: Brenner, U.S. Pat. No. 5,635,400; Brenner et al, Proc. Natl. Acad. Sci., 97: 1665-1670 (2000); Shoemaker et al, Nature Genetics, 14: 450-456 (1996); Morris et al, European patent publication 0799897A1; Wallace, U.S. Pat. No. 5,981,179; and the like. In particular embodiments, a barcode sequence may have a length in range of from 4 to 36 nucleotides, or from 6 to 30 nucleotides, or from 8 to 20 nucleotides.

The term "sequencing", as used herein, refers to a method by which the identity of at least 2 consecutive nucleotides (e.g., the identity of at least 5, at least 10, at least 20, at least 50, at least 100 or at least 200 or more consecutive nucleotides) of a polynucleotide are obtained.

The term "next-generation sequencing" refers to the so-called parallelized sequencing-by-synthesis or sequencing-by-ligation platforms currently employed by Illumina, Life Technologies, and Roche, etc. Next-generation sequencing methods may also include nanopore sequencing methods or electronic-detection based methods such as Ion Torrent technology commercialized by Life Technologies.

As used herein, the terms "antibody" and "immunoglobulin" are used interchangeably herein and are well understood by those in the field. Those terms refer to a protein consisting of one or more polypeptides that specifically binds an antigen. One form of antibody constitutes the basic structural unit of an antibody. This form is a tetramer and consists of two identical pairs of antibody chains, each pair having one light and one heavy chain. In each pair, the light and heavy chain variable regions are together responsible for binding to an antigen, and the constant regions are responsible for the antibody effector functions.

The recognized immunoglobulin polypeptides include the kappa and lambda light chains and the alpha, gamma (IgG$_1$, IgG$_2$, IgG$_3$, IgG$_4$), delta, epsilon and mu heavy chains or equivalents in other species. Full-length immunoglobulin "light chains" (of about 25 kDa or about 214 amino acids) comprise a variable region of about 110 amino acids at the NH$_2$-terminus and a kappa or lambda constant region at the COOH-terminus. Full-length immunoglobulin "heavy chains" (of about 50 kDa or about 446 amino acids), similarly comprise a variable region (of about 116 amino acids) and one of the aforementioned heavy chain constant regions, e.g., gamma (of about 330 amino acids).

The terms "antibodies" and "immunoglobulin" include antibodies or immunoglobulins of any isotype, fragments of antibodies which retain specific binding to antigen, including, but not limited to, Fab, Fv, scFv, and Fd fragments, chimeric antibodies, humanized antibodies, single-chain antibodies, and fusion proteins comprising an antigen-binding portion of an antibody and a non-antibody protein. The antibodies may be detectably labeled, e.g., with a radioisotope, an enzyme which generates a detectable product, a fluorescent protein, a fluorescent molecule, or a stable elemental isotope and the like. The antibodies may be further conjugated to other moieties, such as members of specific binding pairs, e.g., biotin (member of a biotin-avidin specific binding pair), and the like. The antibodies may also be bound to a solid support, including, but not limited to, polystyrene plates or beads, and the like. Also encompassed by the term are Fab', Fv, F(ab')$_2$, and other antibody fragments that retain specific binding to antigen, and monoclonal antibodies.

Antibodies may exist in a variety of other forms including, for example, Fv, Fab, and (Fab')$_2$, as well as bi-functional (i.e. bi-specific) hybrid antibodies (e.g., Lanzavecchia et al., Eur. J. Immunol. 17, 105 (1987)) and in single chains (e.g., Huston et al., Proc. Natl. Acad. Sci. U.S.A., 85, 5879-5883 (1988) and Bird et al., Science, 242, 423-426 (1988), which are incorporated herein by reference). (See, generally, Hood et al., "Immunology", Benjamin, N.Y., 2nd ed. (1984), and Hunkapiller and Hood, Nature, 323, 15-16 (1986)).

An immunoglobulin light or heavy chain variable region consists of a "framework" region (FR) interrupted by three hypervariable regions, also called "complementarity determining regions" or "CDRs". The extent of the framework region and CDRs has been precisely defined (see, "Sequences of Proteins of Immunological Interest" E. Kabat et al., U.S. Department of Health and Human Services, (1991)). The numbering of all antibody amino acid sequences discussed herein conforms to the Kabat system. The sequences of the framework regions of different light or heavy chains are relatively conserved within a species. The framework region of an antibody, that is the combined framework regions of the constituent light and heavy chains, serves to position and align the CDRs. The CDRs are primarily responsible for binding to an epitope of an antigen.

Chimeric antibodies are antibodies whose light and heavy chain genes have been constructed, typically by genetic engineering, from antibody variable and constant region genes belonging to different species. For example, the variable segments of the genes from a rabbit monoclonal antibody may be joined to human constant segments, such as gamma 1 and gamma 3. An example of a therapeutic chimeric antibody is a hybrid protein composed of the variable or antigen-binding domain from a rabbit antibody and the constant or effector domain from a human antibody (e.g., the anti-Tac chimeric antibody made by the cells of A.T.C.C. deposit Accession No. CRL 9688), although other mammalian species may be used.

The term "copy", in the context of a copy of an initial nucleic acid, refers to either the reverse complement of the initial nucleic acid, or a nucleic acid that has the same nucleotide sequence as the initial nucleic acid.

The term "spatial coordinates" refers to coordinates that can be mapped to a specific site on the surface of a substrate. In many cases, the spatial coordinates may be x, y coordinates.

The term "constructing an image" refers to making an image digitally using data points that are each associated with a spatial coordinate.

Other definitions of terms may appear throughout the specification.

DETAILED DESCRIPTION

In order to further illustrate the present invention, the following specific examples are given with the understanding that they are being offered to illustrate the present invention and should not be construed in any way as limiting its scope.

Methods

Provided herein is a method for analyzing a planar cellular sample, e.g., a tissue section or the like. In certain embodiments, the method may comprise: indirectly or directly attaching nucleic acid tags to binding sites in a planar cellular sample. In these embodiments, the nucleic acid tag may itself specifically bind to an epitope in the sample (in which case the attaching is direct and the nucleic acid tag may be a DNA or RNA aptamer). Aptamers are reviewed in, e.g., Radom et al (Biotechnol Adv. 2013 31:1260-74) and Citartan et al (Biosens Bioelectron. 2012 34:1-11), among other publications. In other embodiments, the nucleic acid tag may be tethered to a binding agent, e.g., an antibody, that specifically binds to an epitope in the sample (in which case the attaching is indirect). In these embodiments, the binding agent may be non-covalently (e.g., via a streptavidin/biotin interaction) or covalently linked to an oligonucleotide. An oligonucleotide and the antibody may be linked via a number of different methods, including those that use maleimide or halogen-containing groups, which are cysteine-reactive. Next, the method comprises contacting the planar cellular sample with a solid support comprising an array of spatially addressed features that comprise oligonucleotides. In these embodiments, each oligonucleotide comprises a molecular barcode that identifies the location of the oligonucleotide on the array, i.e., in which "feature" the oligonucleotide is present. In some embodiments, the oligonucleotides of the array may be generally of the formula X-Y, where X is a molecular barcode and Y hybridizes to the nucleic acid tag or complement thereof and can prime nucleic acid synthesis therefrom. Depending on how the method is implemented, the oligonucleotides on the array may comprise one or more repeats (e.g., 2, 3, 4 or 5 or more repeats) of a sequence of formula X-Y, wherein X is a molecular barcode, Y hybridizes to a nucleic acid tag or the complement thereof and, in each repeat, the sequence of Y is different. In these embodiments, the oligonucleotides may contain a cleavable linker between the repeats and each oligonucleotide can be cleaved to produce several oligonucleotides of formula X-Y. Next, the nucleic acid tags, or a copy of the same, may be hybridized to the oligonucleotides of the array to produce duplexes. At this stage of the method, the oligonucleotides do not need to be immobilized on the array. This step of the method may be implemented in a variety of different ways. For example, in certain embodiments, the nucleic acid tags may be copied (e.g., by hybridizing a primer to the tags and copying them using a polymerase), and the copies, once denatured, may locate to the surface of the array whereupon they can hybridize to the oligonucleotides. In other embodiments, the arrayed oligonucleotides (which may be spatially addressed but not physically anchored to the substrate) may hybridize directly with the nucleic acid tags or a copy thereof. Once hybridized to the nucleic acid tags or copy thereof, the oligonucleotides in the duplexes can be extended to produce extension products that each comprises (i) a molecular barcode and (ii) a copy of a nucleic acid tag. The binding site for a nucleic acid tag on the sample can determined by analyzing the sequence of the molecular barcode that is associated with the nucleic acid tag.

In particular embodiments, the array may be made by: (i) synthesizing the oligonucleotides on a solid support, and (ii) cleaving the oligonucleotides from the solid support in the gas phase, thereby producing an array of oligonucleotides that are spatially addressed but not attached to a support. The barcoded oligonucleotides are able to participate in later primer extension reactions without diffusing far from their initial location on the array. Methods for making an array of oligonucleotides and then cleaving the oligonucleotides from the array in the gas phase can be adapted from, e.g., Cleary et al. (Nature Methods 2004 1: 241-248) and LeProust et al. (Nucleic Acids Research 2010 38: 2522-2540). In this example, the oligonucleotides may be cleaved using base (e.g., ammonia or trimethylamine), or photons, for example.

In some cases, the method may involve (e) amplifying the extension products by PCR to produce amplification products. This may be done in situ (i.e., in the planer sample) or, in some embodiments, the extension products may be collected en masse, and then amplified by PCR. After the extension products have been amplified, they can be sequenced to obtain, for each sequenced amplification product, the sequence of a molecular barcode and the sequence of a nucleic acid tag. As would be apparent, the various primers used in the method may contain sequences that are compatible with use in, e.g., Illumina's reversible terminator method, Roche's pyrosequencing method (454), Life Technologies' sequencing by ligation (the SOLiD platform) or Life Technologies' Ion Torrent platform. Examples of such methods are described in the following references: Margulies et al (Nature 2005 437: 376-80); Ronaghi et al (Analytical Biochemistry 1996 242: 84-9); Shendure et al (Science 2005 309: 1728-32); Imelfort et al (Brief Bioinform. 2009 10:609-18); Fox et al (Methods Mol Biol. 2009; 553:79-108); Appleby et al (Methods Mol Biol. 2009; 513: 19-39) and Morozova et al (Genomics. 2008 92:255-64), which are incorporated by reference for the general descriptions of the methods and the particular steps of the methods, including all starting products, reagents, and final products for each of the steps.

In certain embodiments, an image of the planar cellular sample, e.g. a tissue section, can be constructed, where the image shows the binding sites for the attached nucleic acid tags. In these embodiments, for each sequenced extension product, the molecular barcode provides spatial coordinates for the nucleic acid tag that is associated with the molecular barcode. The sequence of the molecular barcode identifies a binding agent, and, thus the sequence of the barcode and the nucleic acid tag allows one to map the binding sites for the binding agents on the planar sample. In some cases, the image produced by the method may show the position and abundance of the attachment sites for the nucleic acid tags. If several different nucleic acid tags are analyzed (e.g., if several different aptamers or oligonucleotide-tagged antibodies are used), the binding sites for the different nucleic acid tags may be color coded so that they are distinguishable from one another by eye. In some cases, the method may further comprise registering the constructed image with an image of the original planar cellular sample, e.g., an image of the planar cellular sample that was taken prior to starting the method. This can be done by, e.g., adding registry features to the planar cellular sample that allow the images to be registered.

As would be apparent, the method may be multiplexed. In these embodiments, the method may comprise indirectly or directly attaching a plurality of different nucleic acid tags to sites in a planar cellular sample, where each binding site (i.e., each binding site for an aptamer or antibody) becomes associated with a different nucleic acid tag.

In some cases, the image may be a false color image, where the colors may correspond to different nucleic acid tags (which, themselves, correspond to different capture agents) and in certain cases, a false color image may be overlayed with or viewed side-by-side with an image of the planar cellular sample that was taken prior to initiating the method (e.g., after hematoxylin and eosin staining).

Certain details of the method are described in greater detail below.

In some embodiments, primer extension or amplification primers in the form of synthetic oligonucleotides derived from the microarray can be contacted directly to the planar cellular sample (e.g., tissue section), by sandwiching the sample between a microarray and a coverslip or other surface. The oligonucleotides in each feature of the array may contain barcoded oligonucleotides, such that the nucleic acid tags present in the sample may be combined with the synthetic oligonucleotides supplied from the array. Thus, the synthetic oligonucleotides can transfer a barcode sequence to the nucleic acid tags, encoding the spatial information present on the microarray through the barcode. In this way the nucleic acid tags from the entire sample (e.g., PCR products, or primer extension products) can be mixed and sequenced, and the spatial information could be reassembled by sequencing the pool and deconvoluting the barcodes (see FIG. 1).

In exemplary embodiments, gaseous ammonia or other non-aqueous method (e.g., photolysis) may be used to cleave the oligonucleotides from the array, leaving each oligonucleotide in its original position. The spatially barcoded oligonucleotides can be combined with magnetic beads, enabling more efficient introduction of the oligonucleotide sequences into the sample, and more efficient capture of the oligonucleotides complexed with the nucleic acids tags in the sample. In certain cases, additional nucleic acids are introduced into the sample that are not necessarily bound to the array; examples of these exogenous nucleic acids include DNA or RNA aptamers, oligonucleotides bound to antibodies, oligonucleotides bound to beads, or oligonucleotides which may function as blocking or splint oligonucleotides. In certain embodiments, one can introduce randomized sequence (e.g., a "counter" sequence; see, e.g., WO201312828) in the barcoded oligonucleotides, in order to use a unique barcode for each individual template molecule.

Figure 2:
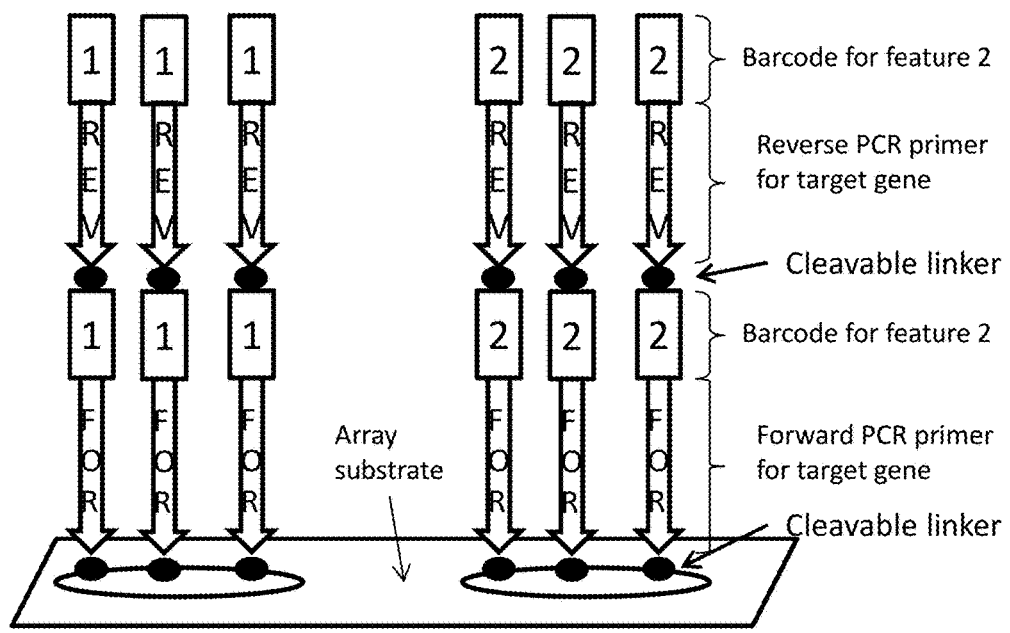
FIG. 2 schematically illustrates two oligonucleotides on an array. This figure shows a schematic of possible design of array sequences to be printed on an array with cleavable linkers that can be cleaved in the gas phase. Each feature cleaves apart into a pair of PCR primers for a nucleic acid tag, and each primer contains a unique barcode sequence associating it with that feature on the array.
Figure 3:
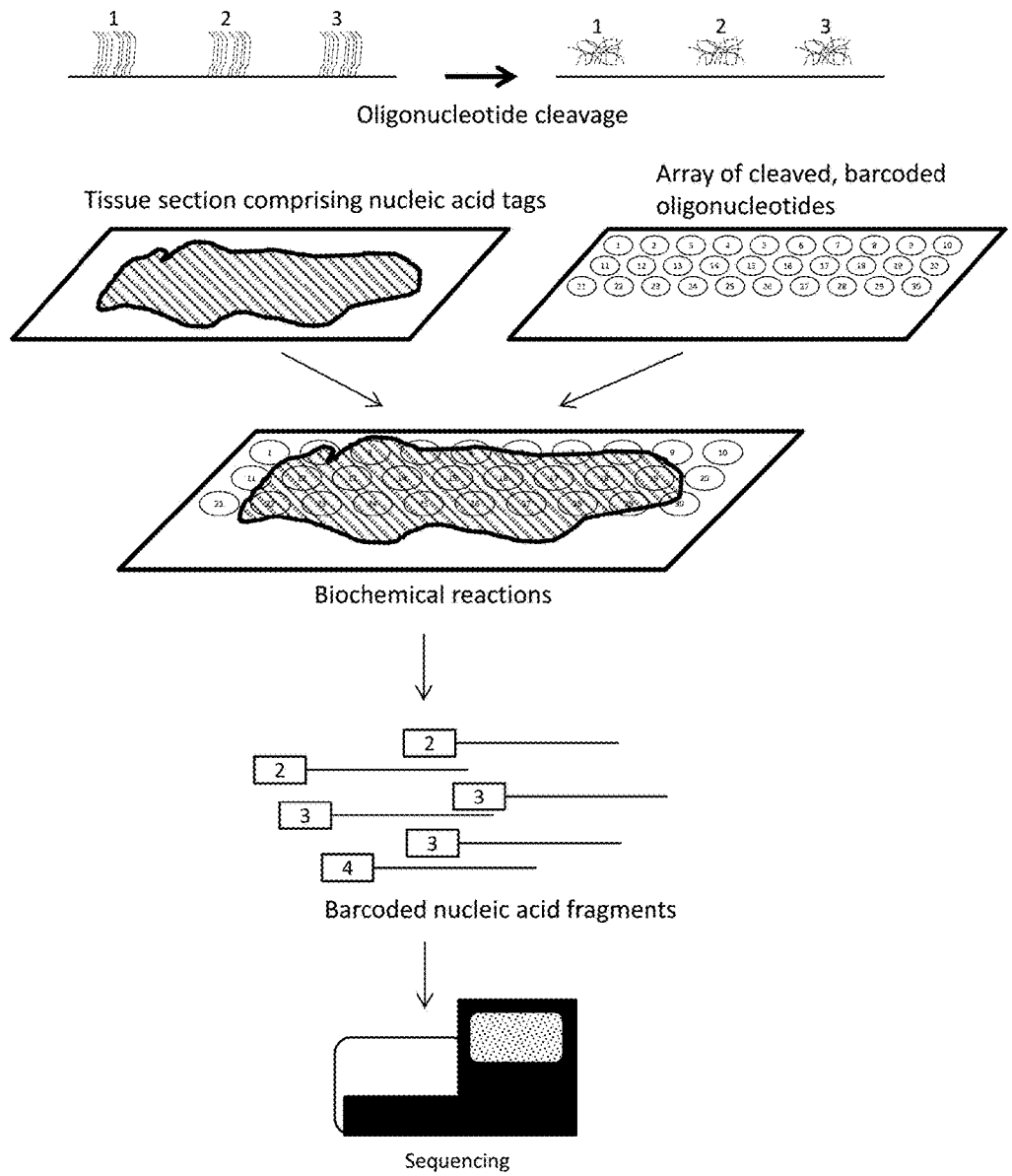
FIG. 3 schematically illustrates a general scheme for using arrays with cleaved, barcoded oligonucleotides to combine spatial information from the array features with sequence information for nucleic acids that are derived from an either native, or pre-processed tissue section. Numerous molecular processes may be employed to generate populations of barcoded nucleic acids, representing native or exogenously applied biomarkers.

In some embodiments, the oligonucleotides are cleaved on the surface of the array and left in place, maintaining spatial positioning in the absence of a covalent linkage between the array substrate and the oligonucleotide (FIGS. 2 and 3). In an exemplary embodiment, oligonucleotide probes are cleaved from the array in the gas phase. Specifically, these embodiments may use gas phase deprotection reagents (e.g. gaseous ammonia or methylamine). These reagents will remove the less labile traditional protecting groups such as benzoyl and isobutyryl, as well as the ultra-labile TAC and PAC. Gas phase reagents eliminate the need to use a non-base cleavable linker. Traditional ester linkers will be cleaved by the gas phase amines, but the lack of aqueous solvents will prevent the oligonucleotide probes from migrating away from their original locations. Deprotection side products can be removed by washing the microarray with a solvent or a solvent mixture of solvents in which the oligonucleotides are not appreciably soluble, such as acetonitrile and toluene, leaving the oligonucleotides in the original discrete locations.

Figure 4:
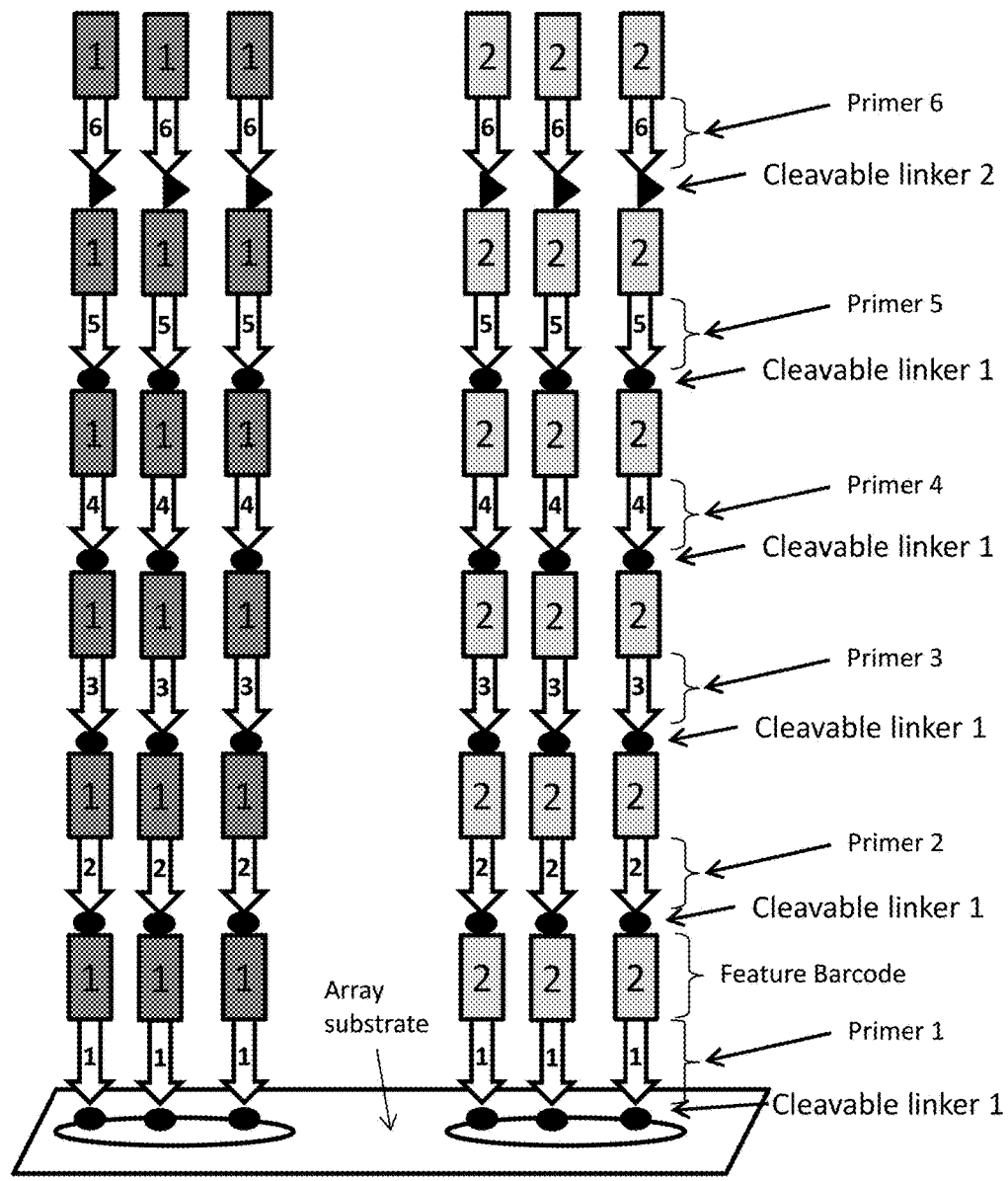
FIG. 4 shows a schematic of array sequences printed on an array with cleavable linkers that can be cleaved in the gas phase. Each feature cleaves apart into a number of PCR primers or other oligonucleotides, and each primer/oligonucleotide contains a unique barcode sequence associating it with that feature on the array. Two types of cleavable linkers can be used to enable cleavage (with two different chemical treatments) at two different times during an experiment. Any number of oligonucleotides/primers can be utilized (i.e. more or less than the 6 shown in this figure).

In some embodiments, it may be advantageous to use more than one cleavable linker or mode of attachment to the array (FIG. 4). For example, an oligonucleotide synthesized on the microarray may contain 2, 3, 4, or more cleavable linkers, such that the oligonucleotide will be cleaved into 3, 4, 5, or more shorter oligonucleotides by the cleavage treatment. This embodiment enables oligonucleotides synthesized in one microarray feature to participate in amplification or primer extension assays on more than one specific target nucleic acid in the sample. For example, one 100 mer oligonucleotide may be cleaved into four 25 mer primers, which may be used to amplify two specific nucleic acid tags by PCR. Also, more than one type of cleavable linker or mode of attachment may be used. In this way, different sets of oligonucleotide probe sequences may be released at different times. For example, treatment with gaseous ammonia may cleave one type of linker, while a second type of linker may be photocleavable. For example, arrays with covalently bound oligonucleotides could be pre-populated with a set of partially complementary oligonucleotides. These hybridized oligonucleotides could be removed by denaturing conditions such as high pH or a temperature above the Tm of the duplex. Alternatively, the covalently bound oligonucleotide probes could be removed by cleavage conditions, either before or after dissociation of the hybridized oligonucleotides. With prudent design of the oligonucleotides, linkers, and conditions, it is possible to allow a variety of sizes of oligonucleotide probes to be removed from the surface of the array in different conditions.

Using this method, a plurality of non-random, defined oligonucleotides can be generated on a substrate such as an array. In some embodiments, an oligonucleotide comprises at least two different subsequences when each of the sequences binds to a different site in a target nucleic acid. In some embodiments, oligonucleotides may comprise both known and randomized, degenerate, or unknown sequences; methods for generating degenerate or randomized sequences are known in the art. Oligonucleotides may comprise at least one, two, three, four, or more, cleavage sites (FIG. 4). Oligonucleotides can be cleaved from the substrate and/or within the sequence at specific cleavage sites by light, heat, a chemical, or enzymes such as RNAses or restriction enzymes. Cleavage chemicals may be applied to the array in liquid or gaseous form. Such cleavage can result in oligonucleotides of varying lengths, including, but not limited to, any length from 15 to 250 base pairs (bp), 18 bp, 25 bp, 30 bp, 35 bp, 40 bp, 50 bp, 60 bp, 70 bp, 75 bp, 80 bp, 90 bp, 100 bp, 110 bp, 115 bp, 120 bp, 125 bp, 130 bp, 140 bp, 150 bp, 175 bp, 200 bp, 225 bp, and/or 250 bp.

In order for the spatial information present in the printed microarray to be transferred to the nucleic acids in the sample, several conditions can be met. First, the oligonucleotide probes on the array should maintain their positions prior to exposure to the sample. This can be achieved by leaving the oligonucleotide probes covalently or otherwise linked to the array, or by cleaving the oligonucleotides with chemicals in the gaseous phase, for example. Second, the nucleic acid tags that are bound to the sample should not diffuse laterally before interacting with the oligonucleotide probes. Third, oligonucleotide probes should interact with the sample in a mode such that there is not excessive lateral diffusion of the oligonucleotide probe sequences before these sequences interact with the nucleic acid tags in the sample. For example, if oligonucleotide probes from one microarray feature were able to diffuse across distances equal to several other features before interacting with the target nucleic acids, the resolution of the spatial information may be compromised. Similarly, it may be preferable to use conditions in which the nucleic acid tags do not have excessive lateral diffusion prior to interacting with the oligonucleotide sequences from the array.

Figure 5:
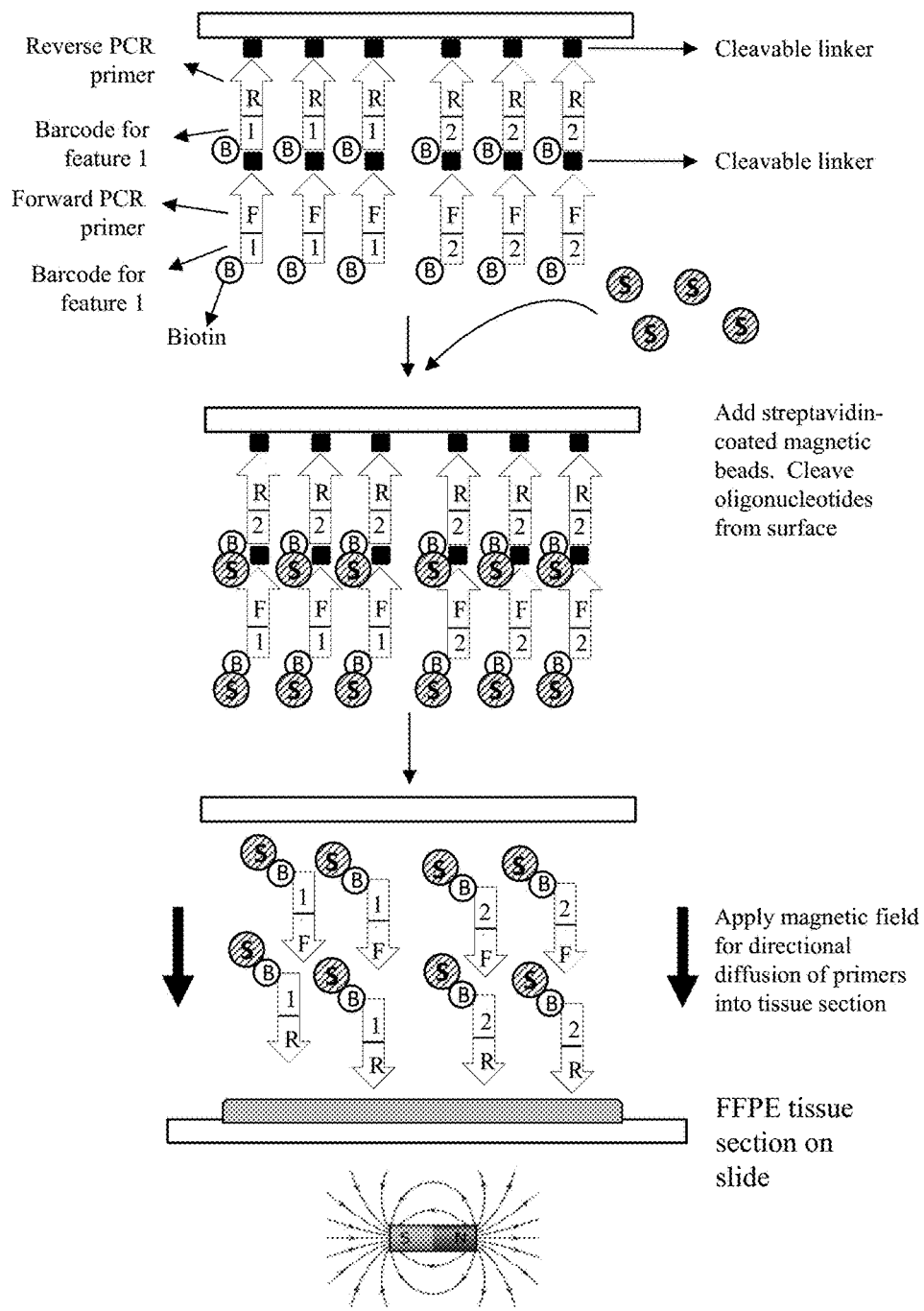
FIG. 5 schematically illustrates how magnetic beads can be used to introduce oligonucleotides to a sample.

To address the problem of lateral diffusion of the oligonucleotide probe or sample nucleic acids, beads can function as a "carrier" between the sample and the microarray surface. In some embodiments, the beads are magnetic beads. For example, streptavidin magnetic beads are superparamagnetic particles covalently coupled to a highly pure form of streptavidin. Suitable magnetic beads include Dynabeads™ available from Life Technologies or Pierce or MagnaBind Magnetic Beads available from Thermo Scientific. The beads could be added to the sample prior to contact with the array, added to the microarray prior to contact with the sample, or added simultaneously when the microarray and sample are contacted. The function of the carrier beads is schematically illustrated in FIG. 5.

In certain embodiments, the oligonucleotides on the surface of the array contain a hapten such as a biotin moiety. The oligonucleotide may be cleaved from the surface of the array using gaseous ammonia, leaving the oligos in place. A slurry of magnetic beads can be added to the entire surface of the sample, such that the beads are evenly distributed over the surface of the sample. Optionally, the magnetic beads can be dried down to the surface of the sample, or held to the surface of the sample with a strong magnetic field. After the sample is contacted by the array with cleaved oligonucleotide probes in a suitable buffer, a magnetic field can be applied to the array such that the magnetic beads are attracted to the surface of the array. Subsequently, the biotin on the cleaved oligonucleotide will be able to interact with the streptavidin on the surface of the magnetic beads. After a short incubation, the magnetic field can be switched such that the bead-oligonucleotide complexes are drawn down to the surface of the sample. Depending on the size of the magnetic particles, the density of the tissue, and the strength of the magnetic field, the magnetic particles may penetrate the sample to a limited extent. The nucleic acids in the sample will then interact with the oligonucleotide on the surface of the bead, transferring the spatial information to the sample nucleic acids or a copy of the sample nucleic acids. For example, in some cases, the sample nucleic acids may be ligated to the oligonucleotide probes. In some cases, an oligonucleotide may act as a primer for reverse transcription of target RNA in the sample. For example, an oligonucleotide may act as a primer in a primer extension reaction. An oligonucleotide probe may act as a PCR primer; in embodiments, additional primers may be added in solution. Each of these examples will create a product nucleic acid that is identical to or complementary to the nucleic acid tag, covalently attached to spatial barcode sequences from the oligonucleotide.

After reaction with the nucleic acid tags in the sample, the extension product will typically remain attached to the magnetic bead. Therefore, after the reaction is complete, the extension product can be extracted from the sample and concentrated using magnetic separation methods. If the nucleic acid tags are attached to the bead-bound oligonucleotides via hybridization, the beads may be further handled under non-denaturing conditions, which may include stringent wash or hybridization conditions. Alternatively, in embodiments where the bead-bound oligonucleotides are primers which are extended using the target nucleic acids as a template, the beads may be further handled under denaturing conditions, which may remove the nucleic acid tags.

In a related embodiment, the magnetic beads may be added to the array surface before cleavage of the oligonucleotide probes, and dried down. If the oligonucleotides are then cleaved by gaseous ammonia, the magnetic beads will remain in place until the sample is contacted with the array.

In a related embodiment, the oligonucleotides from the microarray are not attached to the magnetic beads through a streptavidin-biotin interaction. Instead, magnetic beads with a nucleic acid such as oligo-dT or other sequences can be used, and the oligonucleotides from the array can be designed to hybridize to the nucleic acid on the magnetic beads. In this embodiment, the oligonucleotides could later be removed from the magnetic beads by denaturation. Alternatively, other chemical methods such as click chemistry, thiol chemistry, digoxygenin-antiDig, or other conjugation methods useful for oligonucleotides can be used to attach the oligonucleotide probes to the magnetic beads.

In further embodiments, one can measure the extent of diffusion. For example, in embodiments wherein the oligonucleotides on the array are cleaved into PCR primers, each primer (e.g., both the "forward" and "reverse" primers) may comprise a barcode specifying a microarray feature/spatial location. After amplification by polymerase chain reaction, the barcodes may be identified by sequencing or other methods. If a PCR product has barcodes from the same microarray feature in both the forward and reverse primers, it is likely that both primers did not diffuse far from the array feature they were printed on. However, if a PCR product has a barcode on the forward primer from one feature, and a barcode on the reverse primer from a neighboring feature, this may indicate that the oligonucleotides from one feature diffused sufficiently to prime synthesis near another feature. In the extreme case of complete mixing of the oligonucleotide probes, each PCR product may have different barcodes on the forward and reverse primers, and spatial information would be lost.

There are several possible ways that this method can be implemented, but an overview of the method is described in the following steps. Schematics of the method are shown in the figures.

1. Arrays can be synthesized where each array feature comprises the following elements: a., a cleavable linker allowing removal of the oligonucleotide from the array surface; b., a unique sequence barcode that can be used to associate the oligonucleotide and its amplification products with a particular microarray feature, or set of features; optionally, c., a second "counting" barcode consisting of random or semi-random sequence (such as NNNNNNNN, DDDDDDDD, BBBBBBBB, RRRRRRRR, YYYYYYYY, NNDDBBYY, etc.) and d., a specific primer sequence enabling the amplification or copying of a target sequence. The oligonucleotide sequences may also comprise additional regions, such as barcodes for sample indexing, sequencing adapters, universal sequences for amplification, etc.

2. The primer oligonucleotides would be cleaved from the surface in the gas phase, leaving them in place.

3. The cleaved slide can then be applied to a tissue section (preferably after deparafinization, etc.) that has been bound to binding agents that comprise nucleic acid tags. Other reagents (dNTPs, enzymes, buffer) may also be added in this step. In some embodiments, magnetic beads or exogenous nucleic acids may be added to the sample.

4. The cleaved oligonucleotide would diffuse into the tissue section, and/or the nucleic acid tags (or copies of the same) from the tissue section will diffuse down to the array surface. Conditions will be chosen to allow specific hybridization of the oligonucleotide to the nucleic acid tags. Optionally, exogenous nucleic acids may be added to increase the recovery of desired target sequences.

5. An enzyme such as DNA polymerase (for DNA tags) or Reverse Transcriptase (for RNA tags) will extend the oligonucleotides on the nucleic acid tags, creating a DNA copy of the target nucleic acid attached to the unique barcode sequence that associates the oligonucleotide to a specific feature or region of the microarray. 6. Target amplification (PCR) or copying (primer extension or reverse transcription) may be assayed by in situ fluorescence (e.g., as in qPCR), but in some embodiments, the amplified or copied nucleic acids are washed from the tissue section and collected.

7. Collected nucleic acids are sequenced, after optional library preparation and amplification methods. The sequences obtained should comprise a copy of the nucleic acid tags, as well as 1 or 2 specific barcode sequences associating the sequence with a specific array feature.

8. The spatial information contained in the barcode sequence can be used to overlay specific sequence information onto the image of the section. Precise registration of the microscopic information and the barcodes can be achieved by two or more methods. First, many sections contain regions of connective tissue or blood vessels which would be expected to contain little or no nucleic acids. Second, fiducial features could be used. An example of a fiducial feature would be a fluorescent or optically detectable bead which contains a sequence that can be detected by the spatially barcoded oligonucleotide on the microarray. For example, each fiducial feature may contain a synthetic variant of the target sequence which would be amplified by barcoded PCR primers, and thus each fiducial feature in the image could be matched to a specific microarray feature, registering the orientation and position of the rest of the array features.

Several variations of the method are also provided. In some embodiments, the array oligonucleotides comprise "3' up" oligonucleotides that are not cleaved from the microarray surface initially. 3'-up microarrays are known in the art (Kwiatkowski et al *Nucleic Acids Res* 1999 27: 4710-4714). These oligonucleotides could be extended using the nucleic acid tags as templates, and designed to interrogate single base differences in the tags.

In a second embodiment, 3' up arrays are used, and only one of a pair of PCR primers is cleaved from the surface, while the other primer remains attached to the surface. The first primer could diffuse into the tissue and prime the first strand of synthesis, and this strand could then diffuse back to the surface of the array for second strand synthesis. This embodiment would ensure that the cleaved primers or PCR products would not diffuse too far laterally into adjacent regions. In a variation of this embodiment, uncleaved barcoded 3' up arrays are used, but different from the above embodiment, soluble forward and reverse primers are also added to the tissue section together with the other reagents (dNTPs, enzymes, buffer). While the extension of the primers in presence of the nucleic acid tags could take place in solution within the tissue as well as in the solid phase, under these circumstances, amplification in solution would preferentially occur. However, key to this embodiment is the use of a relatively small amount of one of the soluble primers (e.g., the forward primer, which has the same sequence as the solid phase primer) in such a way that the amplification in solution within the tissue is self-limited. The product of the soluble amplification then diffuses back to the surface, initiating the elongation of the oligonucleotides on the solid phase. In this embodiment: a) the limited amount of amplification in solution decreases the extent of the product diffusion to the adjacent features and b) the initial amplification in solution increases the amount of template for the solid-phase elongation, thus increasing the efficiency of this step. The method described by Hoffmann et al (Lab Chip 2012 12: 3049-3054) may be adapted to the analysis of tissue sections, in the absence of microwells or picowells.

In a third embodiment, the oligonucleotide on the array may be used as primers for reverse transcription. Depending on the concentration of the oligonucleotides and the RNA tags, it may be possible to assay several RNA tags using each microarray feature. For example, using the schematic in FIG. 2, instead of FOR and REV primers, a single oligonucleotide could be cleaved into specific RT primers for 2, 3, 4, or 5 or more different transcripts.

In another embodiment, the oligonucleotides may be cleaved into pairs of PCR primers, and these primers will diffuse into the tissue to prime synthesis from the nucleic acid tags. It is possible that the primers may diffuse laterally, into the adjacent features, contaminating the information by having one barcode associated with >1 feature. However, by requiring that both PCR primers contain the barcode specific for that feature, cross-contamination could be measured. It is unlikely that substantial numbers of both FOR and REV primers from a feature will diffuse into adjacent features to amplify substantial amounts of a tag. Furthermore, this issue may be addressed by limiting the number of PCR cycles done in situ, and further amplifying the isolated PCR products prior to sequencing.

In another embodiment, an apparatus containing microwells may be used. The microwells could be deposited or made on the microarray surface, or possibly on the slide surface of the array-tissue-slide sandwich. The microwells will reduce lateral diffusion of amplification products. PCR amplification may proceed more readily in microwells, and the volume of the wells could be adjusted to optimize primer concentrations. Initial calculations suggest that if each 30 micron microarray feature contains ~0.1 femtomoles of oligonucleotides, these oligonucleotides would be present at tens of micromolar concentrations if they were dispersed into a 4 micron tissue section.

In another embodiment, each feature could comprise a mixture of oligonucleotides to capture sequence from multiple tags, each having the same barcode. For example, a barcode array could be constructed and pre-hybridized with a complex oligonucleotide probe library, wherein each barcode may be associated with primers for 10, 20, 30, or up to 50 or more targets. After hybridizing and washing this array, each microarray feature would contain a mixture of oligonucleotide probes that could be used to assay many nucleic acid tags, and each of those tags will become associated with the barcode for that feature.

In another embodiment, the oligonucleotides may comprise sequencing adapters that are ligated to fragmented mRNA in situ by an RNA ligase such as *Arabidopsis* tRNA ligase or T4 RNA ligase. This method may be used to link the oligonucleotides to the sequences of mRNAs, lincRNAs, or microRNAs present in the tissue.

In another embodiment, exogenous "blocking" nucleic acids may be added to the sample prior to or concomitant with contacting the sample with the array. These nucleic acids may be designed such that they specifically hybridize to, and block subsequent reactions with, common sample nucleic acids such as ribosomal RNA or highly expressed mRNA, thereby allowing the oligonucleotides to hybridize with the nucleic acid tags. For example, oligonucleotides comprising DNA, PNA, or LNA may be designed such that the 3' end cannot be extended by a polymerase, reverse transcriptase, or ligase. If these blocking oligonucleotides bind nucleic acids in the sample, interactions of the probe oligonucleotides from the array with the blocked nucleic acids will be inhibited. In another example, DNA oligonucleotides may be designed to hybridize with undesired RNA sequences in the sample, prior to reaction with RNAseH, which would serve to cleave the undesired RNA sequences. In another example, the exogenous oligonucleotides may comprise DNAzymes or ribozymes which are designed to cleave undesired sequences. Hence, the blocking oligonucleotides may function to suppress the recovery of certain sequences from the sample, thus enriching for the nucleic acid tags.

Figure 6:
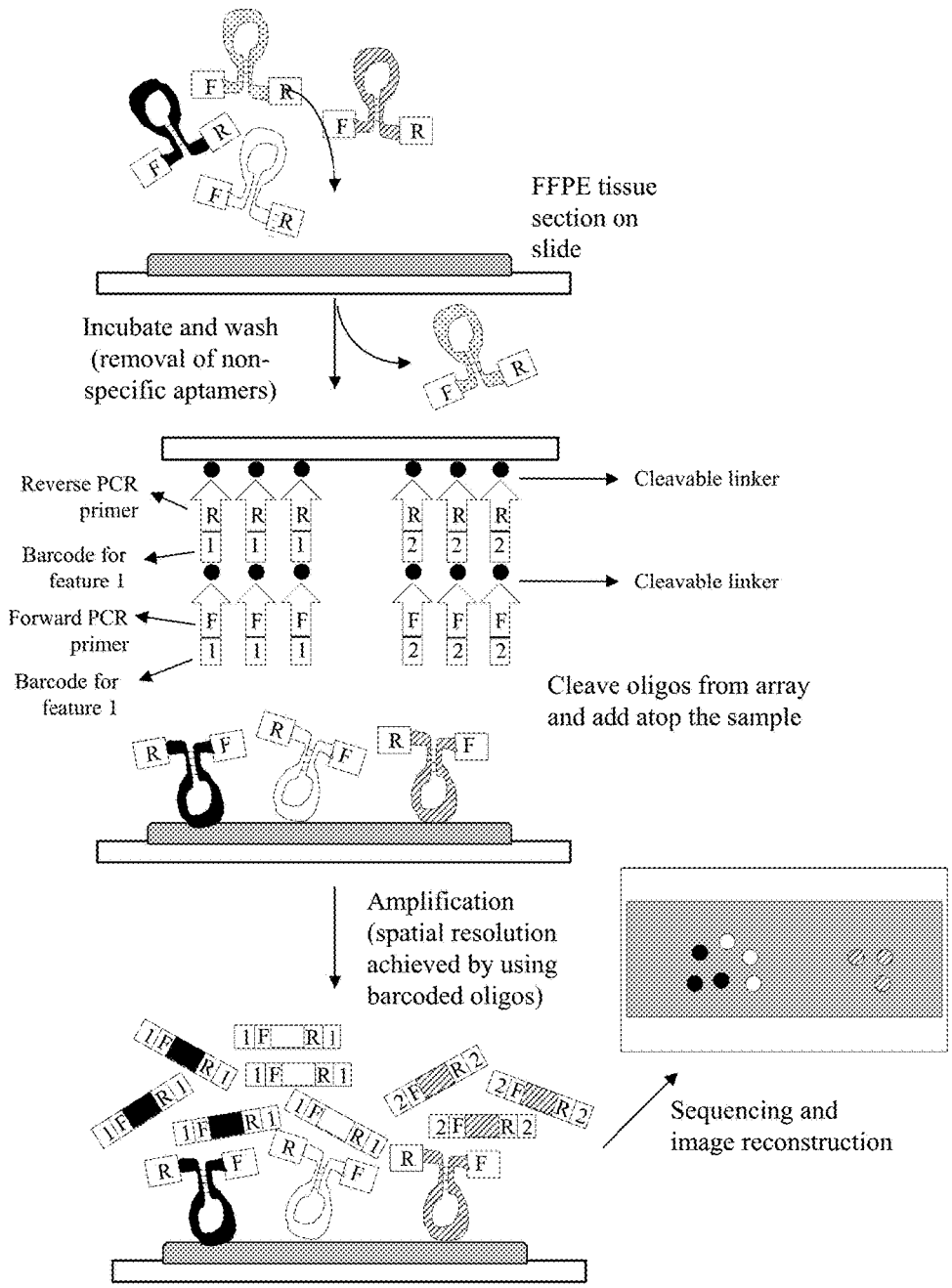
FIG. 6 illustrates how an oligonucleotide array can be combined with DNA or RNA aptamers to detect target analytes with spatial barcoding. In some embodiments, DNA aptamers (horseshoe shapes) may be introduced to the sample to bind target analytes such as proteins. After non-specifically bound aptamers are removed, the remaining aptamers may be combined with the spatially barcoded oligonucleotides from the microarray to create a spatial readout of the aptamer binding.
Figure 7:
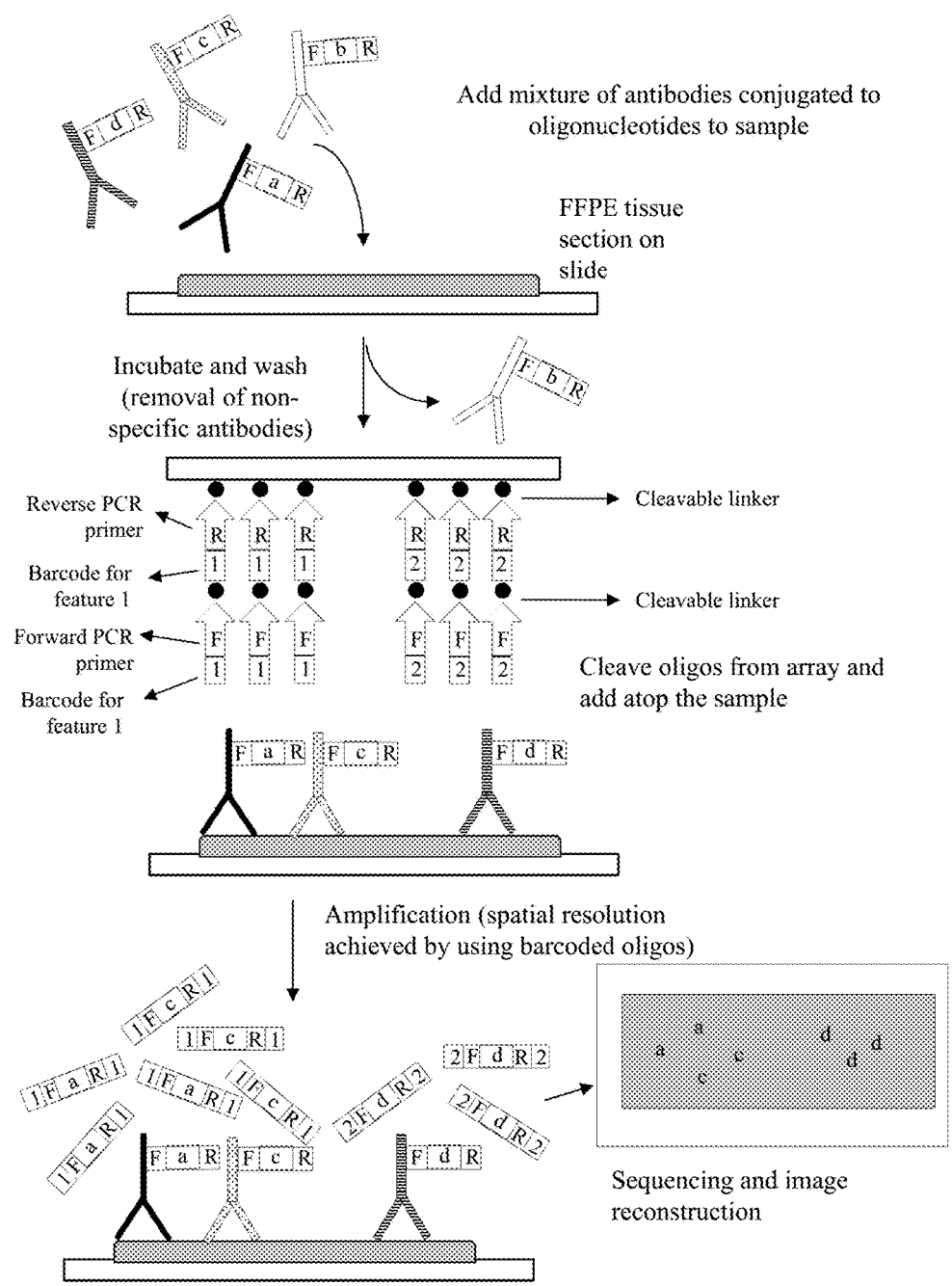
FIG. 7 illustrates how an oligonucleotide array can be combined with antibodies to detect target analytes with spatial barcoding. In some embodiments, oligonucleotide-conjugated antibodies (Y shapes) may be introduced to the sample to bind target analytes such as proteins. After non-specifically bound antibodies are removed, the remaining antibodies may be combined with the spatially barcoded oligonucleotides from the microarray to create a spatial readout of the antibodies' binding.

As noted above, the barcoded oligonucleotide probes are designed to amplify synthetic nucleic acid tags from binding moieties that are bound to specific sites in the tissue section in situ. These tags may report on the presence of non-nucleic acid targets in the sample. Two examples of embodiment are shown in FIGS. 6 and 7. In some embodiments, the nucleic acid tags may comprise DNA or RNA aptamers designed to bind to target analytes such as proteins, peptides, lipids, carbohydrates, etc. (see, e.g., FIG. 6). In some embodiments, nucleic acid tags may be oligonucleotide sequences attached to antibodies (see, e.g., FIG. 7). In some embodiments, the terms nucleic acid tags refer, but not exclusively, to nucleic acid tags from a Proximity Ligation Assay (PLA), nucleic acid-conjugated antibodies, and aptamers. By essentially converting the concentration of a target analyte to a DNA sequence, the present method enables multiplex detection of proteins or other analytes while maintaining spatial information, which is valuable to pathologists. In addition, a combined assay may be envisioned where certain amplified nucleic acids report on the amount or sequence of DNA or RNA targets from the sample (which may be done by hybridizing tagged nucleic acid probes to nucleic acid targets in the sample), and other amplified nucleic acids arise from synthetic oligonucleotide tags which report on the amount of protein or other analyte in the sample. In some embodiments, combined assays may be performed in order to measure the relative amounts of DNA and protein, RNA and protein, DNA methylation, RNA and protein, or other combinations thereof, by converting the relative levels of the target analytes to oligonucleotide tags which can be measured by sequencing.

In certain embodiments, two or more different barcodes are used in a primer. Specifically, the primer sequences may contain a first "specific" barcode of precisely known sequence to identify the spatial region of origin of the amplified, copied, or ligated target nucleic acid. In addition, the primer sequences may contain a second "random" barcode of unknown sequence that would be unique for each primer. Examples of these barcodes include $(N)_6$, $(N)_{10}$, $(N)_{12}$, etc., where "N" indicates a mixture of all four nucleobases. Alternatively, barcodes may be synthesized by mixtures of 2 or 3 nucleobases, e.g., $(R)_6$, $(Y)_{10}$, etc., where R denotes A or G, and Y denotes T or C. Methods of efficiently synthesizing random oligonucleotide sequences are known in the art. If the region of random sequence is sufficiently long, each individual oligonucleotide molecule will have a different sequence (see, e.g., Schmitt et al, Proc Natl Acad Sci USA 2012 109: 14508-14513. Thus, each individual template molecule is likely to be combined with a different random sequence (Fu et al, Proc Natl Acad Sci USA 2011 108: 9026-9031). In later rounds of amplification, common primer regions may be used to amplify all molecules equally. The sequence of this random region of the oligonucleotide will be unknown, but may be decoded during sequencing. In this fashion, if multiple sequencing reads are obtained in a region denoted by the first spatial barcode, the random barcodes may be used to infer how many individual template molecules were sampled, and how many sequencing reads arose from PCR duplicates.

Methods for performing suitable in situ reactions are well known in the art. Examples of methods for performing in situ RT-PCR or in situ PCR reactions are described in the following references: Yap (Nucleic Acids Res 1991 19(15)), Nuovo (Genome Res 1995 4: S151-S167) Nuovo (Methods Mol Biol 2004 287: 261-271), Bagasra Nat Protoc 2007 2: 2782-2795) and Itakura et al (Mod Pathol 2008 21: 326-333), which publications are incorporated by reference.

It will be apparent that any nucleic acid sequencing method may be utilized in the present method. However, the so-called "next generation sequencing" techniques will find particular utility in the method. High throughput sequencing is particularly useful in the methods of the invention because it enables a large number of nucleic acids to be partially sequenced in a very short period of time. For example, each sequencing "read" of the 100 nucleotides should be sufficient to identify both the spatial barcode to which the nucleic acid tag was complexed with (i.e. its location on the array) and the sequence of the nucleic acid tag. As a representative example, the sequencing reaction may be based on reversible dye-terminators, such as used in the Illumina™ technology. Other high-throughput sequencing techniques may be equally suitable for the methods of the invention, e.g. pyrosequencing as illustrated by 454 Technologies, semiconductor sequencing as exemplified by Ion Torrent technologies, Single Molecule Realtime (SMRT™) sequencing as exemplified by Pacific Biosciences technologies, nanopore sequencing methods, or any other sequencing technology that can readily decode a large number of DNA or RNA fragments.

A number of methods of nucleic acid analysis may be used in the analysis step. Typically this may involve sequencing, but it is not necessary to perform an actual sequence determination. For example sequence specific methods of analysis may be used. For example a sequence-specific amplification reaction may be performed, for example using primers which are specific for the spatial barcode and/or for a specific target sequence, e.g. a particular target DNA to be detected (i.e. corresponding to a particular cDNA/RNA or gene or gene variant or genomic locus or genomic variant, etc.). An exemplary analysis method is a sequence-specific PCR reaction.

The method described above allows one to determine which biomarkers are present and at what quantity. The sequencing data contains positional information (i.e., the molecular barcodes) that are used to, e.g., reconstruct an image of the tissue that shows the abundance of the nucleic acid tags in each area of the tissue. In particular embodiments, the method may be performed as a follow up to prior histological analysis of the same planar cellular sample (e.g., after hematoxylin and eosin staining). In these embodiments, the method may comprise analyzing the histology of the planar cellular sample (e.g., using hematoxylin and eosin staining) prior to the labeling step, and then performing the method. In these cases, the analysis may be done if the prior histological analysis is inconclusive. In these embodiments, the method may comprise: performing histological analysis on a cellular sample (e.g., using hematoxylin and eosin staining), and, if the results from this analysis are inconclusive, then analyzing the same cellular sample using the method described above. The additional information provided by the nucleic acid tag analysis may be sufficient to make a clinical decision on the sample.

The planar cellular sample may be a section of a tissue biopsy obtained from a patient. Biopsies of interest include both tumor and non-neoplastic biopsies of skin (melanomas, carcinomas, etc.), soft tissue, bone, breast, colon, liver, kidney, adrenal gland, gastrointestinal tissue, pancreas, gall bladder, salivary gland, cervical, ovary, uterus, testis, prostate, lung, thymus, thyroid, parathyroid, pituitary (adenomas, etc.), brain, spinal cord, ocular tissue, nerve, and skeletal muscle, etc.

In certain embodiments, capture agents specifically bind to biomarkers, including cancer biomarkers, that may be proteinaceous or a nucleic acid. Exemplary cancer biomarkers, include, but are not limited to carcinoembryonic antigen (for identification of adenocarcinomas), cytokeratins (for identification of carcinomas but may also be expressed in some sarcomas), CD15 and CD30 (for Hodgkin's disease), alpha fetoprotein (for yolk sac tumors and hepatocellular carcinoma), CD 117 (for gastrointestinal stromal tumors), CD10 (for renal cell carcinoma and acute lymphoblastic leukemia), prostate specific antigen (for prostate cancer), estrogens and progesterone (for tumor identification), CD20 (for identification of B-cell lymphomas) and CD3 (for identification of T-cell lymphomas).

In particular embodiments, the nucleic acid tags may contain flanking sequences for amplifying the tags by PCR. In these embodiments, the arrayed oligonucleotides may have two or more sections separated by cleavable linkages, wherein at least one of the sections comprises a molecular barcode and the sections, when they are cleaved from the array, provide PCR primers (e.g., forward and reverse primers) that can be used to amplify the nucleic acid tags.

In a particular embodiment, the method may be employed as part of a proximity assay. In this assay, a sample may be bound to two binding agents (e.g., usually two antibodies) that recognize different antigens and that are tagged with different oligonucleotide sequences. When the sequences come in close proximity, they are joined by ligation. The ligation products (which may produce an amplifiable nucleic acid tag) may be investigated using the methods described herein. Some of the general principles of proximity assays are described in, e.g., Söderberg et al Nature Methods 2006 3: 995-1000 and Jarvius et al Molecular & Cellular Proteomics 2007 6: 1500-9).

Kits

Also provided herein are kits for practicing the present method. In certain embodiments, a kit may include: (a) a solid support comprising an array of spatially addressed features that comprise oligonucleotides, wherein each oligonucleotide comprises a molecular barcode that identifies the feature in which the oligonucleotides is present, wherein the oligonucleotides are cleavably linked to the solid support; and (b) a set of binding agents that comprise nucleic acid tags, wherein the oligonucleotides are complementary to a sequence in the nucleic acid tags or the complement of the same. In some embodiments, the oligonucleotides may comprise one or more repeats of a sequence of formula X-Y, wherein X is a molecular barcode and Y hybridizes to a nucleic acid tag or the complement thereof and can be extended using the nucleic acid tag or the complement thereof as a template. A subject kit may also include one or more other reagents for performing the method, e.g., binding buffers and the like.

In addition to above-mentioned components, the subject kit may further include instructions for using the components of the kit to practice the subject method. The instructions for practicing the subject methods may be recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging) etc. In other embodiments, the instructions are present as an electronic storage data file present on a suitable computer readable storage medium, e.g. CD-ROM, diskette, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

Utility

The above-described method can be used to analyze cells from a subject to determine, for example, whether the cell is normal or not or to determine whether the cells are responding to a treatment. In one embodiment, the method may be employed to determine the degree of dysplasia in cancer cells. In these embodiments, the cells may be a sample from a multicellular organism. A biological sample may be isolated from an individual, e.g., from a soft tissue. In particular cases, the method may be used to distinguish different types of cancer cells in FFPE samples. In alternative embodiments, the method described above can be practiced on planar cellular samples that have been fixed in other ways, including planar cellular samples that have been fixed in, e.g., acrolein, glyoxal, osmium tetroxide, carbodiimide, mercuric chloride, zinc salts, picric acid, potassium dichromate, ethanol, methanol, acetone, and/or acetic acid.

The method described above finds particular utility in examining planar cellular samples using a plurality of capture agents, e.g., antibodies, each capture agent recognizing a different marker. Examples of cancers, and biomarkers that can be used to identify those cancers, are shown below. In these embodiments, one does not need to examine all of the markers listed below in order to make a diagnosis.

| Cancer | Markers |
|---|---|
| Acute Leukemia IHC Panel | CD3, CD7, CD20, CD34, CD45, CD56, CD117, MPO, PAX-5, and TdT. |
| Adenocarcinoma vs. Mesothelioma IHC Panel | Pan-CK, CEA, MOC-31, BerEP4, TTF1, calretinin, and WT-1. |
| Bladder vs. Prostate Carcinoma IHC Panel | CK7, CK20, PSA, CK 903, and p63. |
| Breast IHC Panel | ER, PR, Ki-67, and HER2. Reflex to HER2 FISH after HER2 IHC is available. |
| Burkitt vs. DLBC Lymphoma IHC panel | BCL-2, c-MYC, Ki-67. |
| Carcinoma Unknown Primary Site, Female (CUPS IHC Panel - Female) | CK7, CK20, mammaglobin, ER, TTF1, CEA, CA19-9, S100, synaptophysin, and WT-1. |
| Carcinoma Unknown Primary Site, Male (CUPS IHC Panel - Male) | CK7, CK20, TTF1, PSA, CEA, CA19-9, S100, and synaptophysin. |
| GIST IHC Panel | CD117, DOG-1, CD34, and desmin. |
| Hepatoma/Cholangio vs. Metastatic Carcinoma IHC Panel | HSA (HepPar 1), CDX2, CK7, CK20, CAM 5.2, TTF-1, and CEA (polyclonal). |
| Hodgkin vs. NHL IHC Panel | BOB-1, BCL-6, CD3, CD10, CD15, CD20, CD30, CD45 LCA, CD79a, MUM1, OCT-2, PAX-5, and EBER ISH. |
| Lung Cancer IHC Panel | chromogranin A, synaptophysin, CK7, p63, and TTF-1. |
| Lung vs. Metastatic Breast Carcinoma IHC Panel | TTF1, mammaglobin, GCDFP-15 (BRST-2), and ER. |
| Lymphoma Phenotype IHC Panel | BCL-2, BCL-6, CD3, CD4, CD5, CD7, CD8, CD10, CD15, CD20, CD30, CD79a, CD138, cyclin D1, Ki67, MUM1, PAX-5, TdT, and EBER ISH. |
| Lymphoma vs. Carcinoma IHC Panel | CD30, CD45, CD68, CD117, pan-keratin, MPO, S100, and synaptophysin. |
| Lymphoma vs. Reactive Hyperplasia IHC Panel | BCL-2, BCL-6, CD3, CD5, CD10, CD20, CD23, CD43, cyclin D1, and Ki-67. |
| Melanoma vs. Squamous Cell Carcinoma IHC Panel | CD68, Factor XIIIa, CEA (polyclonal), S-100, melanoma cocktail (HMB-45, MART-1/Melan-A, tyrosinase) and Pan-CK. |
| Mismatch Repair Proteins IHC Panel (MMR/Colon Cancer) | MLH1, MSH2, MSH6, and PMS2. |
| Neuroendocrine Neoplasm IHC Panel | CD56, synaptophysin, chromogranin A, TTF-1, Pan-CK, and CEA (polyclonal). |
| Plasma Cell Neoplasm IHC Panel | CD19, CD20, CD38, CD43, CD56, CD79a, CD138, cyclin D1, EMA, kappa, lambda, and MUM1. |
| Prostate vs. Colon Carcinoma IHC Panel | CDX2, CK20, CEA (monoclonal), CA19-9, PLAP, CK 7, and PSA. |
| Soft Tissue Tumor IHC Panel | Pan-CK, SMA, desmin, S100, CD34, vimentin, and CD68. |
| T-Cell Lymphoma IHC panel | ALK1, CD2, CD3, CD4, CD5, CD7, CD8, CD10, CD20, CD21, CD30, CD56, TdT, and EBER ISH. |
| T-LGL Leukemia IHC panel | CD3, CD8, granzyme B, and TIA-1. |
| Undifferentiated Tumor IHC Panel | Pan-CK, S100, CD45, and vimentin. |

In some embodiments, the method may include forwarding data in electronic form to a remote location, where it can be analyzed by a doctor or other medical professional to determine whether a patient has abnormal cells (e.g., cancerous cells) or which type of abnormal cells are present. The data may be used as a diagnostic to determine whether the subject has a disease or condition, e.g., a cancer. In certain embodiments, the method may be used to determine the stage of a cancer, to identify metastasized cells, or to monitor a patient's response to a treatment, for example.

In any embodiment, data can be forwarded to a "remote location," where "remote location" means a location other than the location at which the image is examined. For example, a remote location could be another location (e.g., office, lab, etc.) in the same city, another location in a different city, another location in a different state, another location in a different country, etc. As such, when one item is indicated as being "remote" from another, what is meant is that the two items can be in the same room but be separated, or at least in different rooms or different buildings, and can be at least one mile, ten miles, or at least one hundred miles apart. "Communicating" information references transmitting the data representing that information as electrical signals over a suitable communication channel (e.g., a private or public network). "Forwarding" an item refers to any means of getting that item from one location to the next, whether by physically transporting that item or otherwise (where that is possible) and includes, at least in the case of data, physically transporting a medium carrying the data or communicating the data. Examples of communicating media include radio or infra-red transmission channels as well as a network connection to another computer or networked device, and the interne or include email transmissions and information recorded on websites and the like. In certain embodiments, the image may be analyzed by an MD or other qualified medical professional, and a report based on the results of the analysis of the image may be forwarded to the patient from which the sample was obtained.

EXEMPLARY EMBODIMENTS

A method for analyzing a planar cellular sample is provided. In some embodiments, the method comprises: (a) indirectly or directly attaching nucleic acid tags to binding sites in a planar cellular sample; (b) contacting the planar cellular sample with a solid support comprising an array of spatially addressed features that comprise oligonucleotides, wherein each oligonucleotide comprises a molecular barcode that identifies the location of the oligonucleotide on the solid support; (c) hybridizing the nucleic acid tags, or a copy of the same, with the oligonucleotides to produce duplexes; and (d) extending the oligonucleotides in the duplexes to produce extension products that each comprises (i) a molecular barcode and (ii) a copy of a nucleic acid tag.

In any embodiment, the planar cellular sample may be a formalin-fixed paraffin embedded (FFPE) tissue section.

In any embodiment, the planar cellular sample may be a resin embedded tissue section.

In any embodiment, the planar cellular sample may be a cryosection.

In any embodiment, the planar cellular sample is a layer of cells that has been deposited onto the surface of a planar support by centrifugation.

In any embodiment, the planar cellular sample is a layer of cells that have been grown on a planar support.

In any embodiment, the nucleic acid tags may be attached to antibodies.

In any embodiment, the nucleic acid tags may be RNA or DNA aptamers.

In any embodiment, the method may further comprise: (e) amplifying the extension products by PCR to produce amplification products. This may be done in situ or by collecting the extension products and amplifying them en mass.

In any embodiment, the method may further comprise: (f) sequencing the amplification products to obtain, for each sequenced amplification product, the sequence of a molecular barcode and the sequence of a nucleic acid tag.

In any embodiment, the method may further comprise (g) constructing an image of planar cellular sample showing the binding sites for the attached nucleic acid tags, wherein, for each sequenced extension product, the molecular barcode provides spatial coordinates for the associated nucleic acid tag.

In these embodiments, the image may show the position and abundance of the attachment sites for the nucleic acid tags.

In any embodiment, the nucleic acid tags may be the product of a proximity ligation assay.

In any embodiment, the array may be made by: (i) synthesizing the oligonucleotides on a solid support, and (ii) cleaving the oligonucleotides from the solid support in the gas phase, thereby producing an array of oligonucleotides that are spatially addressed but not attached to a support.

In any embodiment, the oligonucleotides on the array may have two or more sections separated by cleavable linkages, wherein at least one of the sections comprises the molecular barcode and the sections, when they are cleaved from the array, provide PCR primers that amplify the nucleic acid tags.

In any embodiment, the oligonucleotides on the array may comprise one or more repeats of a sequence of formula X-Y, wherein X is the molecular barcode and Y hybridizes to the nucleic acid tags or the complement thereof.

In any embodiment, the method may comprise: (i) copying the nucleic acid tags and (ii) hybridizing the copy of the nucleic acid tags with the oligonucleotides to produce duplexes.

In any embodiment, the method may further comprise registering the constructed image with an image of the original planar cellular sample. In some cases this may be done using register features that were added to the planar cellular sample prior to analysis.

In any embodiment, the method may comprise overlaying the constructed image with an image of the original planar cellular sample.

In any embodiment, the tissue section may be a tissue biopsy.

In any embodiment, the method may comprise indirectly or directly attaching a plurality of different nucleic acid tags to sites in a planar cellular sample, wherein each site is associated with a different tag.

A kit for analyzing a planar sample is provided. In some embodiments, the kit comprises (a) a planar support (e.g., a glass slide) comprising an array of spatially addressed features that comprise oligonucleotides (e.g., at least 100, at least 500, at least 1,000, at least 5,000, at least 10,000, at least 50,000, at least 100,000 or at least 500,000 or more features, each containing a different oligonucleotide), wherein each oligonucleotide comprises a molecular barcode (e.g., a DNA sequence that is in the range of 5 to 50 or 6 to 30 nucleotides in length) that identifies the feature in which the oligonucleotide is present, wherein the oligonucleotides are cleavably linked to the solid support, e.g., by a gas or photocleavable linkage; and (b) a set of binding agents that comprise nucleic acid tags, wherein the oligonucleotides are complementary to a sequence in the nucleic acid tags or the complement of the same.

In any kit embodiment, the binding agents may be aptamers.

In any kit embodiment, the binding agents may be antibodies.

In any kit embodiment, the oligonucleotides may have a randomized sequence in addition to the molecular barcode.

In any kit embodiment, there may be at least 2, at least 5, at least 10, or at least 20 or more binding agents in the kit.

In any kit embodiment, the oligonucleotides may comprise one or more repeats (e.g., 1, 2, 3, 4, 5, 6, 7, 8 or more repeats) of a sequence of formula X-Y, wherein X is a molecular barcode, Y hybridizes to a nucleic acid tag or the complement thereof, and the sequence of Y is different for each repeat. In these embodiments, the oligonucleotides can be cleaved to produce one or more primers of sequence X-Y.

It will also be recognized by those skilled in the art that, while some embodiments have been described, the invention is not limited thereto. Various features and aspects of the above disclosure may be used individually or jointly. Further, although certain embodiments have been described in the context of its implementation in a particular environment, and for particular applications those skilled in the art will recognize that its usefulness is not limited thereto and that the present disclosure can be beneficially utilized in any number of environments and implementations. Accordingly, the claims set forth below should be construed in view of the full breadth and spirit of the invention as disclosed herein.

What is claimed is:
1. A method of processing a sample, comprising:
    (a) indirectly or directly attaching nucleic acid tags to binding sites in a planar cellular sample;
    (b) contacting the planar cellular sample with a solid support comprising an array of spatially addressed features that comprise oligonucleotides, wherein each oligonucleotide comprises a molecular barcode that identifies the location of the oligonucleotide on the solid support and wherein the array is made by
        (i) synthesizing the oligonucleotides on a solid support, and
        (ii) cleaving the oligonucleotides from the solid support in the gas phase,
    to produce an array of oligonucleotides that are spatially addressed but not attached to the support;
    (c) hybridizing the nucleic acid tags, or a copy of the same, with said oligonucleotides to produce duplexes; and
    (d) extending the oligonucleotides in said duplexes to produce extension products that each comprises (i) a molecular barcode and (ii) a copy of a nucleic acid tag or a complement thereof.

2. The method of claim 1, further comprising:
    (e) amplifying the extension products by PCR to produce amplification products.

3. The method of claim 2, further comprising:
    (f) sequencing the amplification products to obtain, for each sequenced amplification product, the sequence of a molecular barcode and the sequence of a nucleic acid tag.

4. The method of claim 3, further comprising:
    (g) constructing an image of the planar cellular sample showing the binding sites for the attached nucleic acid tags, wherein, for each sequenced extension product, the molecular barcode provides spatial coordinates for the associated nucleic acid tag.

5. The method of claim 4, wherein the image shows the position and abundance of the attachment sites for the nucleic acid tags.

6. The method of claim 1, wherein said nucleic acid tags are attached to antibodies.

7. The method of claim 1, wherein said nucleic acid tags are RNA or DNA aptamers.

8. The method of claim 1, wherein said nucleic acid tags are the product of a proximity ligation assay.

9. The method of claim 1, wherein the oligonucleotides have two or more sections separated by cleavable linkages, wherein at least one of the sections comprises said molecular barcode and the sections, when they are cleaved from the array, provide PCR primers that amplify the nucleic acid tags.

10. The method of claim 1, wherein the oligonucleotides comprise one or more repeats of a sequence of formula X-Y, wherein X is the molecular barcode and Y hybridizes to the nucleic acid tags or the complement thereof.

11. The method of claim 1, wherein the method comprises (i) copying the nucleic acid tags and (ii) hybridizing the copy of the nucleic acid tags with said oligonucleotides to produce duplexes.

12. The method of claim 1, further comprising registering the constructed image with an image of the original planar cellular sample.

13. The method of claim 12, wherein the registering is assisted by register features that were added to the planar cellular sample prior to analysis.

14. The method of claim 1, wherein said nucleic acid tags or said oligonucleotides are attached to magnetic beads.

15. The method of claim 1, wherein said planar cellular sample is an FFPE tissue section.

16. The method of claim 15, wherein said tissue section is a tissue biopsy.

17. The method of claim 1, wherein the method comprises indirectly or directly attaching a plurality of different nucleic acid tags to sites in a planar cellular sample, wherein different tags are attached to a plurality of binding agents designed to bind to two or more classes of target molecules, said classes comprising DNA, RNA, proteins, oligosaccharides, and lipids.

* * * * *

UNITED STATES PATENT AND TRADEMARK OFFICE
CERTIFICATE OF CORRECTION

PATENT NO. : 9,834,814 B2
APPLICATION NO. : 14/493127
DATED : December 5, 2017
INVENTOR(S) : Brian Jon Peter et al.

Page 1 of 1

It is certified that error appears in the above-identified patent and that said Letters Patent is hereby corrected as shown below:

In the Specification

In Column 4, Line 51, delete "that that" and insert -- that --, therefor.

In Column 4, Line 60, delete "that that" and insert -- that --, therefor.

In Column 13, Line 54, delete "deparafinization," and insert -- deparaffinization, --, therefor.

In Column 14, Lines 4-8, delete "6. Target amplification (PCR) or copying (primer extension or reverse transcription) may be assayed by in situ fluorescence (e.g., as in qPCR), but in some embodiments, the amplified or copied nucleic acids are washed from the tissue section and collected." and insert the same in Column 14, Line 5 as a new paragraph.

In Column 21, Line 34, delete "interne" and insert -- internet --, therefor.

Signed and Sealed this
Twenty-ninth Day of May, 2018

Andrei Iancu
*Director of the United States Patent and Trademark Office*